(12) United States Patent
Oakberg

(10) Patent No.: US 6,473,181 B1
(45) Date of Patent: Oct. 29, 2002

(54) MEASUREMENT OF WAVEPLATE RETARDATION USING A PHOTOELASTIC MODULATOR

(75) Inventor: Theodore C. Oakberg, Forest Grove, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 0 days.

(21) Appl. No.: 09/463,532
(22) PCT Filed: Jul. 24, 1998
(86) PCT No.: PCT/US98/15173
§ 371 (c)(1),
(2), (4) Date: Jan. 21, 2000
(87) PCT Pub. No.: WO99/05488
PCT Pub. Date: Feb. 4, 1999

Related U.S. Application Data
(60) Provisional application No. 60/053,890, filed on Jul. 28, 1997.

(51) Int. Cl.$^7$ ................................................ G01J 4/00
(52) U.S. Cl. ...................................... 356/365; 356/364
(58) Field of Search ................................. 356/364, 365, 356/366, 367, 368, 382, 450, 453, 491; 250/225, 226

(56) References Cited

U.S. PATENT DOCUMENTS

| | | | |
|---|---|---|---|
| 3,902,805 A | 9/1975 | Redner | 356/33 |
| 4,362,387 A | 12/1982 | Clark | 356/338 |
| 4,400,062 A | 8/1983 | Mori | 350/406 |
| 4,480,916 A | 11/1984 | Bareket | 356/351 |
| 4,725,145 A | 2/1988 | Azzam | 356/367 |
| 4,801,798 A | 1/1989 | Lange | 250/225 |
| 4,904,931 A | 2/1990 | Miller | 324/96 |
| 4,973,163 A | 11/1990 | Sakai | 356/367 |
| 5,072,111 A | 12/1991 | Gilino | 250/227.15 |

(List continued on next page.)

OTHER PUBLICATIONS

Kemp, J.; Piezo–Optical Birefringence Modulators: New Use for a Long–Known Effect; Journal of the Optical Society; vol. 59, No. 8, pp 950–954 (Aug. 1969).
Hinds Instruments; PEM–90 Photoelastic Modulators; Brochure; 10 pages; 1991.
Oakberg, T.; Linear Birefringence and Optical Rotation; Application Note; 5 pages; 1993.
Wang, B. An Improved Method for Measuring Low–Level Linear Birefringence in Optical Materials;SPIE Inorganic Optical Materials Proceedings; vol. 3424; 1998.
Schellman J. et al; Optical Spectroscopy of Oriented Molecules; Chem. Rev. vol. 87, pp1359–1399; May, 1987.
Frattini & Fuller; Phase–Modulated Flow Birefringence; Journal of Rheology; vol. 28; Feb. 1984.
Ohmi et al; High Sensitivity Two–Dimensional Thermal–and Mechanical–stress–Induced Birefringence Measurements in a Nd:Yag Rod.

*Primary Examiner*—Michael P. Stafira
(74) *Attorney, Agent, or Firm*—Ipsolon LLP

(57) ABSTRACT

A practical system and method for measuring waveplate retardation. The system employs a photoelastic modulator (22) in an optical setup and provides high sensitivity. The analysis is particularly appropriate for quality-control testing of waveplates (26). The system is also adaptable for slightly varying the retardation provided by a waveplate (26) or any other retarder device in a given optical setup. To this end, the waveplate (26) position may be precisely altered to introduce correspondingly precise adjustments of the retardation values that the waveplate (26) provides. The system is further refined to permit one to compensate for errors in the retardation measurements just mentioned. Such errors may be attributable to static birefringence present in the optical element of the photoelastic modulator (22) that is incorporated in the system.

8 Claims, 1 Drawing Sheet

U.S. PATENT DOCUMENTS

| | | | |
|---|---|---|---|
| 5,268,741 A | 12/1993 | Chou | 356/351 |
| 5,311,284 A | 5/1994 | Nishino | 356/364 |
| 5,457,536 A | 10/1995 | Kornfiled | 356/366 |
| 5,532,823 A | 7/1996 | Fukui | 356/364 |
| 5,536,936 A | 7/1996 | Devillon | 250/226 |
| 5,652,673 A | 7/1997 | Oakberg | 359/308 |
| 5,792,049 A | 8/1998 | Eppstein | 600/306 |
| 5,825,492 A | 10/1998 | Mason | 356/345 |
| 5,864,403 A | 1/1999 | Ajii | 356/365 |
| 5,900,939 A | 5/1999 | Aspnes et al. | 356/369 |
| 5,956,147 A | 9/1999 | Jellison, Jr. | 356/369 |
| 6,023,332 A | 2/2000 | Bergstrom et al. | 356/365 |
| 6,055,053 A | 4/2000 | Lesniak | 356/366 |
| 6,078,042 A | 6/2000 | Fellows | 250/252.1 | ately precise adjustments of the retardation values that the waveplate provides.

MEASUREMENT OF WAVEPLATE RETARDATION USING A PHOTOELASTIC MODULATOR

This application claims the benefit of U.S. provisional application No. 60/053,890, filed Jul. 28, 1997.

TECHNICAL FIELD

This application relates to a system and process for precise measurement and adjustment of waveplate retardation using a photoelastic modulator.

BACKGROUND

A waveplate is an optical device that resolves a linear polarized light wave into two orthogonal, linear polarized components and produces a phase shift between them. Thus, the polarization state of the light beam is altered. Waveplates, which are often referred to as retarders, are useful in applications requiring control or analysis of the polarization states of light.

In some applications it is necessary to measure or calibrate the retardardation of a waveplate that is used in an experimental or analytical optical setup. Such calibration will account for any variations from the specified retardation of a particular waveplate.

Moreover, in some instances it may be desirable to vary slightly the retardation provided by a waveplate that is used in an optical setup, without replacing or physically modifying the waveplate.

SUMMARY OF THE INVENTION

The present invention is directed to a practical system and method for measuring waveplate retardation. The system employs a photoelastic modulator in an optical setup and provides high sensitivity. The analysis is particularly appropriate for quality-control testing of waveplates.

The system of the present invention is also adaptable for slightly varying the retardation provided by a waveplate (or any other retarder device) in a given optical setup. Such "fine tuning" of the retardation provided by the waveplate is useful in high-precision analyses. To this end, the waveplate position may be precisely altered to introduce correspondingly precise adjustments of the retardation values that the waveplate provides.

The present invention is further refined to permit one to compensate for errors in the retardation measurements just mentioned. Such errors may be attributable to static birefringence present in the optical element of the photoelastic modulator that is incorporated in the system.

BEST MODES FOR CARRYING OUT THE INVENTION

Figure 1:
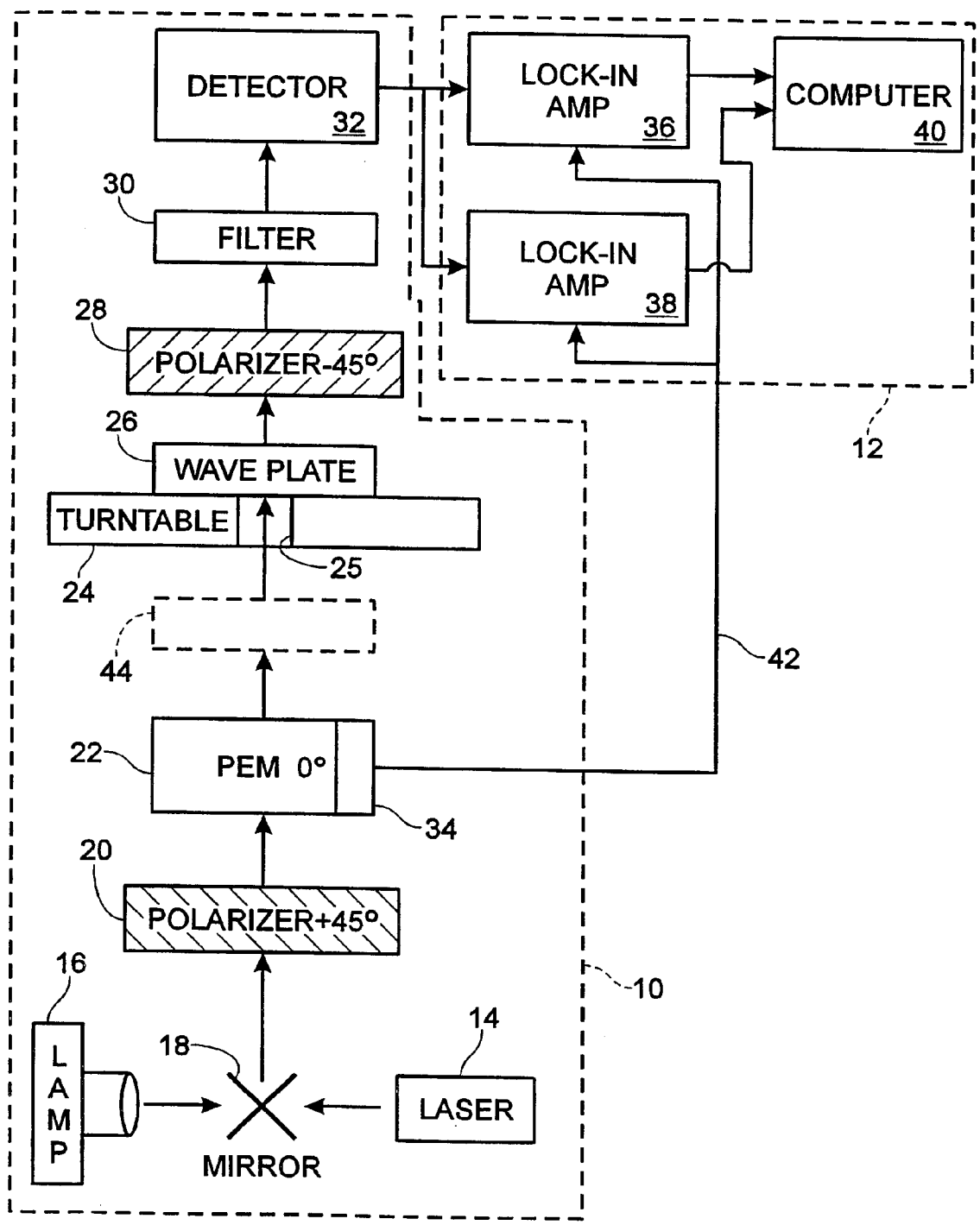
FIG. 1 is a diagram of a preferred embodiment of the present system.

The diagram of FIG. 1 depicts an optical setup 10 and associated signal processing components 12 for carrying out the present invention. The setup includes a polarized HeNe laser as a light source 14. This light source is useful for measuring the accuracy of waveplates that are designed for light wavelengths in the range of 633 nanometers (nm).

A second light source 16 is used in instances where waveplates designed for other wavelengths, say 900 nm, are to be tested. This source may be a tungsten halogen incandescent lamp. The wavelength selection is made by placing a narrow-band filter 30 immediately before the hereafter-described detector 32. For 900 nm, a suitable filter is available from Oriel Instruments, Strafford, Conn. as Model No. 57710. Alternatively, a laser with a different wavelength may be used.

A movable mirror 18 is, for convenience, located between the two light sources 14, 16 to enable one to easily switch between sources. The mirror directs the light to the remaining components of the optical setup, as described next. In a preferred embodiment, those components are arranged in a vertical alignment.

The source light is directed to be incident on a first polarizer 20 that is oriented at ±45° relative to a baseline axis. A Glan-Thompson calcite polarizer is preferred.

The polarized light from the first polarizer 20 is incident on the optical element of a photoelastic modulator. In a preferred embodiment the photoelastic modulator (hereafter referred to as a PEM) is one manufactured by Hinds instruments, Inc., of Hillsboro, Oreg., Model I/FS50. The optical element of this device includes a 1°-wedge angle between the two opposing surfaces to eliminate modulated interference effects, as explained in U.S. Pat. No. 5 5,652,673. The laser 14 may be rotated to control the intensity of the light incident on the PEM.

A controller 34 imparts oscillating birefringence to the optical element of the PEM 22. The oscillating birefringence introduces a phase difference between the orthogonal components of the polarized light that propagates through the PEM. At any instant in time the phase difference is the retardation introduced by the PEM, which, in addition to being a function of time, is also dependent on the thickness of its optical element and the refractive indices in the two orthogonal axes. The retardation is measurable in units of length, such as nanometers or wavelengths.

The PEM controller 34 is adjustable to allow one to vary the amplitude of the retardation introduced by the PEM. In the case at hand, the retardation amplitude is selected to match that of the waveplate 26 under study, which, for the purposes of this description, is a quarter-wave waveplate. That is, the peak retardation introduced by the waveplate 26 is specified to be one-fourth of the wavelength of light passing through it. The PEM is oriented with its axis at 0°.

The waveplate 26 under study (also referred to as the "subject" waveplate) is placed on a turntable 24 that has a central aperture 25 to permit the light emanating from the PEM to reach the waveplate 26. One suitable turntable is that manufactured by Newport Corporation of Irvine Calif. as a waveplate/polarizer holder GM-1R, which features 360° rotation with a sensitivity of 5 arcmin.

The light emanating from the waveplate 26 passes though another Glan-Thomson polarizer 28 that has its axis oriented at −45°. The light thus reaches the detector 32 (here assuming that the laser light source 14 is in use, thus the filter 30 is removed from the setup).

The detector 32 is a PIN-type silicon photoconductive type with a close-coupled transimpedence preamplifier mounted in the same enclosure. Before turning to the detector output signal processing, it is useful set forth the time-dependent relationship between the retardation of the subject waveplate 26 and the intensity of the light reaching the detector. The pertinent expression is:

$$I(t) = \frac{KI_o}{2}[1 - \cos(B + A_o\cos(\Omega t)] \quad (1)$$

Where:

I=intensity of light at the detector 32;
$I_0$=intensity of linearly polarized light incident on the PEM 22;
K=a factor accounting for transmission losses, excluding light rejected by the second polarizer 28;
$A_0$=PEM retardation amplitude in radians;
$\Omega=2\pi$=angular frequency of the PEM oscillations; and
B=the waveplate retardation, in radians.

Expansion of equation 1 in a Fourier series results in the following expressions for the first and second harmonic terms of the Fourier series:

$$I_f = KI_O \sin(B) J_1(A_0) \quad (2)$$

$$I_{2f} = KI_O \cos(B) J_2(A_0) \quad (3)$$

These two equations are sufficient for the determination of the retardation between 0 and half-wave for the wavelength of light used in the measurement. (Such waveplates are called "zero order" waveplates.) From equations 3 and 4, one must choose an equation for which the trigonometric factor (sin or cos) is significantly less than 1.

Using source light having the design wavelength of the zero-order subject waveplate, the equation for the present, quarter-wave plate 26 is:

$$B_q = \cot^{-1}\left[\frac{I_{2f}J_1(A_o)}{I_{1f}J_2(A_o)}\right] \quad (4)$$

In instances where a half-wave plate is used as the subject waveplate, the retardation is expressed as:

$$B_h = \tan^{-1}\left[\frac{I_{1f}J_2(A_0)}{I_{2f}J_1(A_o)}\right] \quad (5)$$

In the foregoing equations (4) and (5), the terms $J_1$ and $J_2$ are the first and second order Bessel functions. The PEM amplitude is unrestricted, except that values that yield either $J_1$ or $J_2$ close to zero are to be avoided.

The components for processing the signal output from the detector 32 include signal recovery devices in the form of two lock in amplifiers 36, 38. One device 36 made by EG&G Inc. of Wellesley, Mass., model number PAR 5105, suffices for detection of the signal component at the frequency f of the PEM, which frequency is provided by the PEM controller as a reference signal via line 42 to both lock-in amplifiers 36, 38.

A somewhat more sensitive lock-in amplifier 38 is used to extract the second harmonic component 2f inasmuch as the presence of the strong 1f signal tends to overwhelm the 2f signal. An EG&G model PAR 5302 may be used for this purpose. The relative sensitivities of the two amplifiers 36, 38 were determined by measuring the strong If signal simultaneously with both lock-in amplifiers.

An alternative to two lock-in amplifiers is to use a single lock-in amplifier under computer control to sequentially measure $I_{1f}$ and $I^{2f}$.

Equation (4) may be written in more practical form, in terms of the AC first and second harmonics signals $V_{2f}$ and $V_{1f}$ on the output of the detector (and using the relation $\tan^{-1}+\cot^{-1}=\pi/2$) as:

$$B \text{ (radians)} = \frac{\pi}{2} - \tan^{-1}\left[\frac{J_1 V_{2f}}{J_2 \text{abs}[V_{1f}]}\right] \quad (6)$$

To prepare the lock-in amplifiers, an auto-phase operation is performed on the 2f amplifier 38 without the waveplate 26 in the setup. Then, the waveplate 26 is located with its fast axis approximately parallel to the PEM axis and an auto-phase operation is performed with the if lock-in 36.

The DC signals from the amplifiers 36 and 38 are provided to a computer workstation 40 for calculating the retardation B in accord with Equation (6). In this regard, the waveplate 26 is located on the turntable 24, and the turntable 24 is rotated. The computer 40 notes the value ($V_{2f}$) of the received 2f signal at each interval of the turntable rotation and identifies the greatest absolute value of $V_{2f}$. The minimum positive $V_{2f}$ signal (or maximum negative $V_{2f}$ signal) is received when one of the waveplate's birefringent axes (fast or slow) is oriented parallel to the axis of the PEM. A positive value of $V_{2f}$ indicates that the waveplate retardation is less than quarter-wave (for the present subject waveplate). If that value is negative, the subject waveplate retardation is greater than quarter-wave.

The auto-phase operation mentioned above establishes the sign convention for determining whether the detected birefringent axis of the waveplate is fast or slow. Thus, if the algebraic sign of the detected $V_{1f}$ signal is positive, it is the fast axis of the waveplate that is parallel to the axis of the PEM. If the algebraic sign of the detected $V_{1f}$ signal is negative, the slow axis of the waveplate is parallel to the axis of the PEM.

The expression:

$$\Delta = -\tan^{-1}\left[\frac{J_1 V_{2f}}{J_2 \text{abs}[V_{1f}]}\right] \quad (7)$$

is convenient for noting the deviation of the measured retardation from true quarter-wave (in this example) retardation. Either the retardation B or the deviation $\Delta$ may be expressed in units of length, such as nanometers, by multiplication by $\lambda/2\pi$.

The foregoing processing can be carried out via the computer 40, as mentioned. Moreover, the turntable 24 may be connected to a stepper motor arrangement whereby the computer is provided with suitable drivers for controlling the rotation of the turntable during the measurement process.

Alternatively, the computer monitor may be used to provide a visual indication of the received $V_{2f}$ signal (whereby the lock-in amplifier can be set to provide output in X-Y format, with the X values being the signals of interest). An operator can manually rotate the turntable as the signals are observed on the computer monitor.

Measurement of the retardation of the waveplate using one wavelength of light, $\lambda_1$, may be used to calculate the retardation at another wavelength, $\lambda_2$, provided that the difference in the orthogonal refractive indices ($n_x-n_y$) is known with precision as a function of the wavelength of light.

Many waveplates are made which are "multiple order." That is, the actual retardation of the waveplate in waves has the form:

B(waves)=n+$B_{nominal}$(waves).

Quartz is an intrinsically birefringent material that is suitable for making such waveplates.

For example, a waveplate with a retardation of 10¼ waves (multiple order) and a waveplate with a retardation of ¼ wave will give identical results in many optical setups. The method described above for single-order waveplates may be extended to the measurement of multiple-order waveplates if the thickness of the waveplate and ($n_x$-$n_y$) vs. $\lambda$ is known. (The thickness can be determined by mechanical means, such as using a micrometer.) Alternatively, measurement of the waveplate retardation using two different wavelengths of light would provide the information necessary to calculate the actual (multiple-order) retardation without ambiguity.

As noted above, the foregoing setup and signal processing is particularly amenable for quality control testing of manufactured waveplates. Moreover, with the retardation of the waveplate so precisely determined, there may be instances where it is desirable (such as in experimental situations) to adjust the retardation of the light emanating from the waveplate. One may wish to make the adjustment for canceling the above-mentioned deviation $\Delta$. To this end, the present invention employs the tilting feature of the above-described turntable 24. As is known in the art, the retardation characteristics of waveplates (especially multiple order waveplates) are sensitive to the angle of incidence of the light that propagates through them. In the preferred embodiment this sensitivity is exploited by measured tilting of the turntable 24, thus changing the incidence angle of the light reaching the waveplate. Such motion is carried out until, for example, the deviation value $\Delta$ goes to zero, thereby effectively correcting the performance of the waveplate.

Use of a PEM in the above-described setup offers a practical and efficient way of measuring waveplate retardation. As noted, the oscillating birefringence of the PEM's optical element is relied on for this purpose. Such elements, however, have a small residual or static birefringence that imparts a corresponding static component of retardation in the measurement, thus introducing an error. As another aspect of the invention, this error is eliminated by a compensation technique described next.

The compensation technique involves mounting a waveplate 44 (shown in dashed lines in FIG. 1) after the PEM 22. This waveplate has a known one-half wavelength retardation and is referred to as a half-wave plate. The half-wave plate is mounted in a turntable like the one 24 described above, while the subject waveplate 26 is removed from the setup. The half-wave plate 44 is rotated until the $V_{1f}$ signal from the lock-in amplifier 36 is minimized. Then the half-wave plate 44 is tilted until that signal becomes zero. This established the net retardation of the PEM and half-wave plate at the corrected magnitude and angle.

Before proceeding with the corrected setup just described, it is necessary to adjust the overall setup in order to maintain the validity of equations (1)–(7) above. The validity is lost because of the polarization effects that are introduced by the compensating half-wave plate. In this regard, the linear polarization components of the light will be rotated through 90°, and the sense of the circular components will be reversed (e.g., right circular polarized will become left circular polarized). The adjustment for these effects (hence the restoration of the validity of the equations) is accomplished by rotating the second polarizer 28 by 90°.

It is contemplated that, Instead of using a half-wave plate for the compensation or correction technique just described, one can substitute a full-wave plate. This would avoid the half-wave plate polarization effects mentioned above. Use of a full-wave plate requires a two-axis tilting turntable, and the full-wave plate is mounted with its axes parallel to those tilt axes. The mounted full-wave plate is positioned in the setup (again, the subject waveplate is not present) with one of its axes parallel to the PEM axis. For this configuration, a large $V_{2f}$ signal will be observed, along with a small $V_{1f}$ signal. The full-wave plate is tilted until $V_{1f}$ becomes zero.

Next, the second polarizer 28 is rotated to −90°. The $V_{2f}$ signal will become very small or vanish. If both $V_{1f}$ and $V_{2f}$ are zero, the compensation adjustment is complete. That is, the PEM static retardation is parallel to the PEM axis. If $V_{1f}$ and/or $V_{2f}$ are not zero, the full-wave plate should be rotated until $V_{2f}$ is zero, then tilted until $V_{1f}$ is zero. Some iteration may be needed to complete the compensation technique.

While the present invention has been described in terms of preferred embodiments, it will be appreciated by one of ordinary skill in the art that modifications may be made without departing from the teachings and spirit of the foregoing. As such, the scope of the invention is defined in the following claims and their equivalents.

What is claimed is:

1. An apparatus for measuring retardation induced by a subject optical element that exhibits birefringence, comprising:
    a source of polarized light arranged such that the light propagates along a path from the source;
    a light detector located in the path substantially opposite the source;
    a photoelastic modulator located in the path between the source and detector such that the light propagates through part of the photoelastic modulator, wherein the photoelastic modulator exhibits static birefringence,
    a compensating optical element rotatably mounted between the photoelastic modulator and the subject optical element and adjustable to compensate for the static retardation of the photoelastic modulator; and
    the subject optical element being rotatably mounted in the path so that the light propagating through the part of the photoelastic modulator propagates through the subject optical element to be incident on the light detector, wherein the retardation of the subject optical element correlates to the intensity of the light that is incident on the detector, and whereby the detector produces an output signal indicative of the intensity.

2. The apparatus of claim 1 comprising means for processing the detector output signal to provide a measure of the retardation of the subject optical element and to compare the measured retardation with a predetermined retardation associated with the subject optical element.

3. The apparatus of claim 2 wherein the subject optical element is a waveplate.

4. The apparatus of claim 1 including means for mounting the compensating optical element in the optical path for selectively tilting the compensating optical element.

5. A method of operating an optical system for measuring retardation induced by a subject optical element, comprising the steps of:
    rotatably mounting the subject optical element in a path of polarized light that emanates from a source;
    locating a photoelastic modulator in the path between the source and the subject optical element such that the light propagates through the photoelastic modulator and through the subject optical element;
    controlling the photoelastic modulator to induce retardation into the light passing through it;
    processing the light that passes through the subject optical element to determine the difference between the retardation induced by the subject optical element and that induced by the photoelastic modulator; and compensating for static retardation present in the photoelastic modulator by introducing a rotatably mounted compensating optical element into the system between the photoelastic modulator and the subject optical element.

6. The method of claim 5 wherein the compensating step includes the step of selectively tilting the compensating optical element that is introduced into the system between the photoelastic modulator and the subject optical element optical element.

7. The method of claim 5 wherein the introducing step includes introducing a half-waveplate as the compensating optical element and accounting for the polarization effects of the half waveplate.

8. The method of claim 5 wherein the introducing step includes introducing a full-waveplate as the compensating optical element.

\* \* \* \* \*